Figure 1:
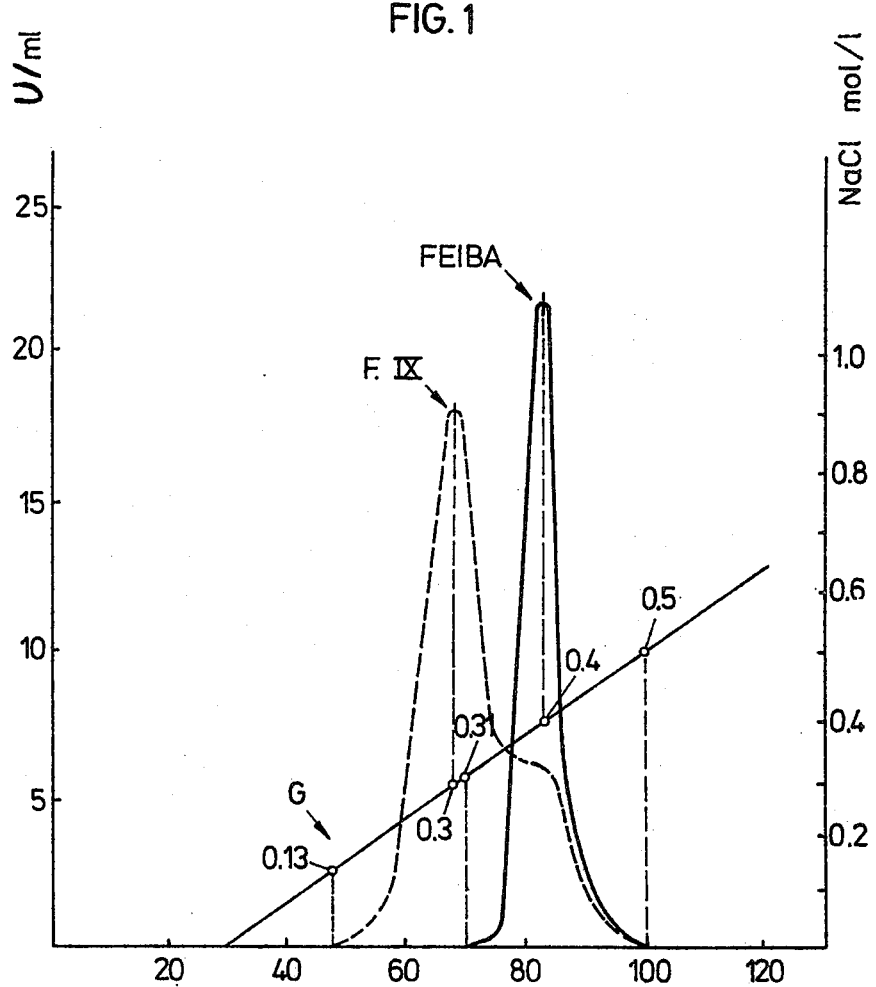

United States Patent [19]

Eibl et al.

[11] 4,395,396

[45] Jul. 26, 1983

[54] BLOOD-COAGULATION-PROMOTING PREPARATION BASED ON HUMAN PROTEINS AND A METHOD OF PRODUCING THE SAME

[75] Inventors: Johann Eibl; Otto Schwarz; Fritz Elsinger, all of Vienna; Anton Philapitsch, Ebenfurt, all of Austria

[73] Assignee: Immuno Aktiengesellschaft für Chemisch-medizinische Produkte, Vienna, Austria

[21] Appl. No.: 283,143

[22] Filed: Jul. 14, 1981

[30] Foreign Application Priority Data

Jul. 22, 1980 [AT] Austria ................................. 3781/80

[51] Int. Cl.³ ........................................... A61K 35/14
[52] U.S. Cl. .................................................. 424/101
[58] Field of Search ......................................... 424/101

[56] References Cited

U.S. PATENT DOCUMENTS 4,160,025  7/1979  Eibl et al. .
4,170,590  10/1979 Stephan et al. .
4,286,056  8/1981  Andary et al. ........................ 435/3
4,287,180  9/1981  Thomas .............................. 424/101

FOREIGN PATENT DOCUMENTS 359645  7/1978   Austria .
2715832  5/1979  Fed. Rep. of Germany .
1092754  11/1967 United Kingdom .

OTHER PUBLICATIONS

Pepper, D. S., et al., "Chromatography of Human Prothrombin Complex of Dextran Sulphate Agarose", Thrombosis Research, vol. 11, pp. 687-692, 1977.

Proc. Natl. Acad. Sci., U.S.A., vol. 74, No. 7, pp. 3028-3032, Jul. 1977 Medical Sciences.

Gitel, G. N. et al., "In Vitro and in Vivo Correlation of Clotting Protease Activity: Effect of Heparin", Proc. Natl. Acad. Sci. USA, vol. 74, No. 7, pp. 3028-3032, Jul. 1977.

Alving, B. M. et al., "Hypotension Associated with Prekallikrein Activator (Hageman-Factor Fragments) in Plasma Protein Fraction", New England Journal of Medicine, pp. 66-70, Jul. 13, 1978.

Elsinger, F., Speech Delivered on Activated Prothrombin Complex Concentrates, The State of the Art of Managing Hemophilia with Factor VIII Inhibitor, Rome, Mar. 30-31, 1981.

Primary Examiner—Sam Rosen
Attorney, Agent, or Firm—Brumbaugh, Graves, Donohue & Raymond

[57] ABSTRACT

In a method of producing a blood-coagulation-promoting preparation based on human proteins and having a content of coagulation factors II, VII, IX and X and factor-VIII-inhibitor-bypassing-activity (FEIBA), human plasma is treated with sulphated high-polymer carbohydrates and/or with basic ion exchangers, the protein mixture with generated FEIB-activity is adsorbed on the ion exchanger, and the preparation is gained by elution and concentration.

14 Claims, 2 Drawing Figures

BLOOD-COAGULATION-PROMOTING PREPARATION BASED ON HUMAN PROTEINS AND A METHOD OF PRODUCING THE SAME

The invention relates to a blood-coagulation-promoting preparation based on human proteins, having a content of coagulation factors II, VII, IX and X and factor-VIII-inhibitor-bypassing-activity.

Blood-coagulation-promoting preparations exhibiting factor-VIII-inhibitor-bypassing-activity, in short "FEIBA" (Factor-Eight-Inhibitor-Bypassing-Activity), are known. In U.S. Pat. No. 4,160,025 the production of such a preparation is described. It is successfully applied for the treatment of patients suffering from haemophilia A and whose blood contains an inhibitor directed against factor VIII. The chemical structure of the FEIBA factor so far has been unknown. It is only known that a protein having a molecular weight of approximately 100,000 is involved. The production of the preparation according to the above-mentioned patent specification was carried out by generation from human plasma containing citrate ions in the absence of free calcium ions by treatment with water-insoluble inorganic coagulation-physiologically-surface-active substances, such as silicagel or kaolin, and subsequent adsorption and elution, wherein a mixture of factors II, VII, IX and X, of factor FEIBA and of other proteins is obtained, whose composition has not been described so far.

Although, as mentioned above, the preparation according to U.S. Pat. No. 4,160,025 has proved valuable for the treatment of factor VIII inhibitor patients, there is the task of enlarging the sphere of application and further improving the safety of FEIBA preparations, in particular of reducing to a minimum undesired side reactions, such as thrombogenic and vasoactive effects.

This object is achieved according to the invention with a blood-coagulation-promoting preparation based on human proteins and having a content of coagulation factors II, VII, IX and X and a factor-VIII-inhibitor-bypassing-activity, which preparation is characterized in that it is free of thrombogenic activity up to at least 2 units of FEIBA per ky rabbit in the thrombosis inducing activity test according to Wessler, it is free of kallikrein activity and free of prekallikrein activator activity—measured in an aqueous solution of the preparation with a FEIBA concentration of up to at least 10 units per ml, it is affinity-chromatographically separable on dextran sulphate agarose by means of an NaCl gradient in a manner that the protein with factor IX activity elutes at a lower NaCl concentration than the protein with FEIB-activity, the eluates containing the protein with factor IX activity and the protein with FEIB-activity contain $\alpha$- and $\beta$-globulins when electrophoretically separated, the separation curve comprising in the $\alpha$-globulin region a main peak corresponding to 60 to 80% of the total protein, a shoulder of 10 to 20% of the total protein following thereupon, as well as a slightly pronounced peak in the $\beta$-globulin region corresponding to a content of 10 to 20% of the total protein following upon the shoulder-like course of the separation curve.

The above-defined characteristic features of the preparation, i.e. the absence of thrombogenic activity and of kallikrein activity or prekallikrein activator activity—the latter being resposible for vasoactive effects—, suggest that the preparation has an excellent safety. The thrombosis inducing activity test and the tests on kallikrein activity and prekallikrein activator activity are known to one skilled in the art. They will be described in more detail after the Examples.

The third characteristic feature of the preparation according to the invention, i.e. the separability by way of affinity-chromatography on dextran sulphate agarose by means of an NaCl gradient is illustrated in FIG. 1 of the drawings by way of an example. The method of affinity-chromatography on dextran sulphate agarose is known to one skilled in the art (D. S. Pepper and C. Prowse, Thrombosis Research 11 (1977), 687–692). Dextran sulphate (molecular weight 500,000) is coupled to CNBr-activated sepharose 4 B (Pharmacia Fine Chemicals AB, Uppsala, Sweden). The dextran sulphate sepharose thus obtained is equilibrated in a 0.4% trisodiumcitrate.2H$_2$O solution (pH=7.4) and filled into a column. The sample to be examined is applied onto the column and then fractionally eluted with an NaCl solution in 0.4% trisodiumcitrate.2H$_2$O (pH=7.4) with an increasing NaCl concentration.

In FIG. 1 the fraction numbers of the eluates are plotted on the abscissa. On the left ordinate the activities of the coagulation factors are plotted in units per ml and on the right ordinate the concentration of the sodium chloride gradient is plotted in mol/l. The linear course of the gradient is entered as line G. As can be seen from FIG. 1, the protein with factor IX activity elutes in the region of 0.1 to 0.5 molar NaCl, with a maximum at 0.3 molar, the protein with FEIB-activity elutes in the region of 0.3 to 0.5 molar NaCl, with a maximum of 0.4 molar. The increasing NaCl concentration is revealed by the NaCl gradient G reaching from 0 molar to 0.65 molar NaCl.

Figure 2:
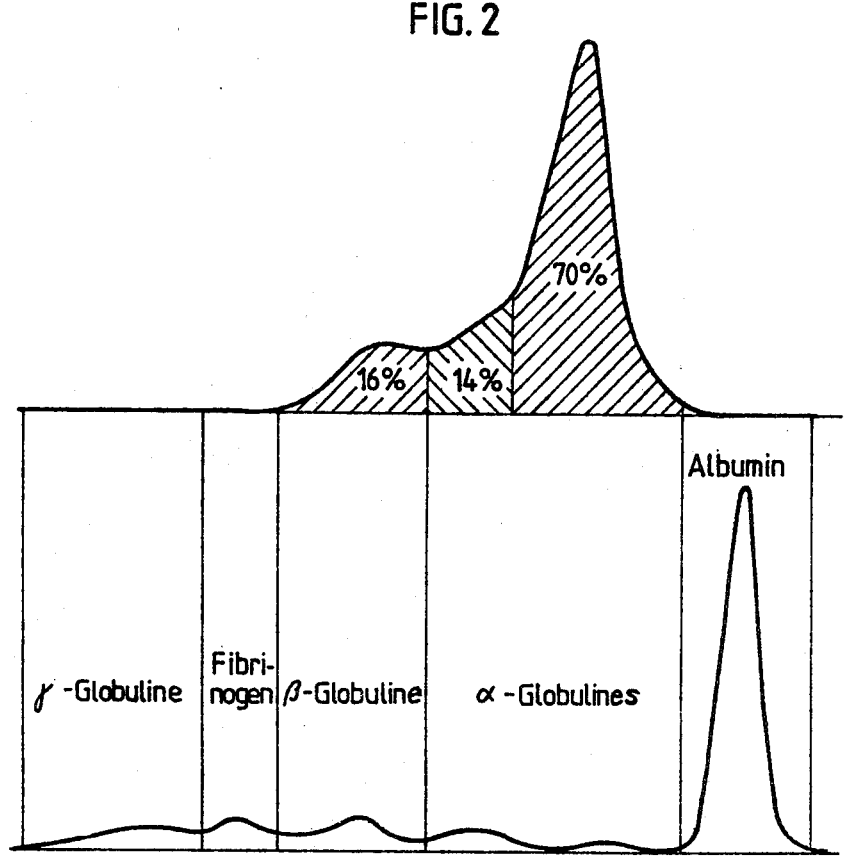

Finally, as the fourth characteristic feature of the preparation according to the invention also the content of globulins when electrophoretically separated is typical, which is explained by way of FIG. 2 of the drawings. The upper section of FIG. 2 illustrates, by way of an example, the separation curve of the eluates of the dextran sulphate sepharose chromatography according to the invention containing proteins with factor IX activity and with FEIB-activity, whereas the lower section of FIG. 2 reflects the electrophoretic separation curve of a native human plasma. It is revealed that, in this example, the main peak in the $\alpha$-globulin region amounts to 70% of the total protein. Upon the main peak a shoulder follows in the $\alpha$-globulin region, amounting to 14% of the total protein content, whereupon a slightly pronounced peak, which amounts to 16% of the total protein, follows upon the shoulder in the $\beta$-globulin region.

Advantageously a further characteristic feature of the preparation according to the invention resides in the fact that the FEIB-activity, after a one-hour incubation in factor VIII inhibitor plasma, is preserved by at least 50%. This property indicates a longer lasting efficacy when applied to factor VIII inhibitor patients.

Advantageously a further characteristic of the preparation according to the invention resides in the fact that the factor IX activity, after a one-hour incubation in factor IX deficient plasma, is preserved by at least 50%. This means that the preparation contains little or only a very slight portion of activated factor IX. It is known that activated factor IX is inactivated in human plasma. Activated factor IX would cause detrimental thrombogenic effects. It is known from the literature (Proc. Natl. Acad. Sci. USA, Vol. 74, No. 7, 3028–3032, July 1977, "In vitro and in vivo correlation of clotting protease activity: Effect of heparin" by S. N. Gitel, R. C. Stephenson and S. Wessler) that it is exactly factor IXa that possesses the highest thrombogenic efficacy as opposed to other activated coagulation factors, such as Xa and IIa (thrombin).

Finally, one characteristic of the blood-coagulation-promoting preparation according to the invention advantageously is to be seen in that it comprises a content of inter-alpha-trypsin-inhibitor (ITI) of 0.05 to 5 mg per FEIBA unit.

The content of ITI causes the thrombogenicity of the preparation of the invention to be low in the Wessler test.

Furthermore, the invention relates to a method of producing the new blood-coagulation-promoting preparation based on human proteins and having a content of the coagulation factors II, VII, IX and X and a factor-VIII-inhibitor-bypassing-activity, which method is characterized in that human plasma is treated with sulphated, high-polymer carbohydrates and/or with basic ion exchangers, and the protein mixture with generated FEIB-activity is adsorbed, whereupon it is recovered by elution and concentration.

When carrying out the method it is to be taken care that the plasma and the reactants be kept free from substances that are capable of increasing the antithrombin III activity, such as heparin or heparinoids.

According to one embodiment of the invention the plasma at first is briefly treated with sulphated, high-polymer carbohydrates, the protein mixture with generated FEIB-activity is then adsorbed on an ion exchanger based on dextran and eluted and concentrated immediately thereupon.

According to another embodiment of the invention the plasma is treated with an ion exchanger on dextran basis; after at least two hours of exposure the protein mixture with generated FEIB-activity, adsorbed on the ion exchanger, is eluted and then concentrated. With this embodiment, the generation of the FEIB-activity depends on the period of exposure. This may last up to 48 hours.

The individual steps of the production process are not critical and may vary within a large range; thus, the pH may be between 6 and 9, the temperature may amount to between 0° and 40° C., the amounts of dextran sulphate used may be between 0.1 and 500 mg/l plasma, and DEAE-Sephadex may be used to an amount of between 0.01 to 10 g/l plasma. As a starting material for the method of the invention, not only native human plasma, but also plasma fractions, e.g. cryosupernatant and Cohn-I-supernatant (8% alcohol) may be used.

The preparation according to the invention and the method for its production will be explained in more detail by the following Examples, the methods of determination applied being explained and the results being shown in the Tables following the Examples.

EXAMPLE 1

1,000 l of fresh frozen human citrated plasma are thawed at 0° to +4° C. and the resulting cryoprecipitate is separated by centrifugation at +2° C. To the resulting "cryosupernatant" 10 g of dextrane sulphate (molecular weight 500,000) are added at a negative pH of 7.7 and stirred for 15 minutes at +4° C., with the substance FEIBA being generated.

Thereafter 500 g of the anion exchanger DEAE-Sephadex A-50 (Pharmacia Fine Chemicals AB, Uppsala, Sweden) are added and stirred at +4° C. for half an hour, the generated FEIBA substance together with the factors of the prothrombin complex (II, VII, IX, X) and inert proteins being adsorbed on the insoluble DEAE-Sephadex.

The DEAE-Sephadex is separated immediately after the adsorption procedure by centrifugation or filtration; the supernatant plasma may be used for recovering gamma-globulin and albumin.

The DEAE-Sephadex is subjected to a double washing process; at first the DEAE-Sephadex is stirred with 50 l of a solution consisting of 4 g/l trisodiumcitrate.2-$H_2O$, 7 g/l sodium chloride and 18 g/l disodium hydrogen phosphate.$12H_2O$ in distilled water, pH 7.5, for 15 minutes at +4° C. After separation by filtration the DEAE-Sephadex is stirred with 50 l of a solution consisting of 4 g/l trisodiumcitrate .$2H_2O$ and 7 g/l sodium chloride in distilled water, pH 7.5, for 15 minutes at +4° C. and then again is separated by filtration.

For elution the DEAE-Sephadex is stirred with 25 l of a solution consisting of 30 g/l sodium chloride and 1 g/l trisodiumcitrate .$2H_2O$ in distilled water, pH 7.0, for 20 minutes at +4° C. The eluate containing the generated FEIBA substance, the factors of the prothrombin complex (II, VII, IX, X) as well as inert protein, is gained by filtration, the DEAE-Sephadex is discarded. The eluate is dialyzed over night against 1,000 l of distilled water at +4° C., then frozen and subjected to a first lyophilization process. In the resulting bulk material the FEIB-activity is determined according to the method described in U.S. Pat. No. 4,160,025.

For the production of the pharmaceutically applicable preparation with FEIB-activity the bulk material is dissolved in so much distilled pyrogen-free water that the FEIB-activity amounts to between 10 and 50 FEIBA units per ml (in the present case 25 FEIBA unit per ml). After the addition of the salts required for establishing isotonicity and adjusting the pH to between 7.0 and 7.5 the solution is cleared through membrane filters and at last is sterile-filtered through a 0.2 μm membrane filter. The solution is filled into the final containers under sterile conditions in 20 ml portions, deepfrozen and lyophilized.

EXAMPLE 2

1,000 l fresh frozen human citrated plasma are thawed at 0° to +4° C. and the resulting cryoprecipitate is separated by centrifugation at +2° C. To the resulting "cryosupernatant" 500 g of the anion exchanger DEAE-Sephadex A-50 (Pharmacia Fine Chemicals AB, Uppsala, Sweden) are added at a native pH of 7.7 and stirred for half an hour at +4° C., the factors of the prothrombin complex (II, VII, IX, X) and inert proteins being adsorbed on the DEAE-Sephadex.

Thereafter the mixture is allowed to stand for 12 hours at +4° C.; during this "contact time" the FEIBA substance is generated.

The DEAE-Sephadex, after a 12-hour "contact time," is separated by centrifugation or filtration; the supernatant plasma may be used for recovering gamma-globulin and albumin.

The further processing of the DEAE-Sephadex (double washing, elution etc.) is effected in the same manner as described in Example 1.

The thrombosis inducing activity test according to Wessler, which is described in the literature, i.e. in J.Appl. Physiol. 14 (1959), 943–946, "Biologic Assay of a Thrombosis Inducing Activity in Human Serum" by Stanford Wessler, Stanley M. Reimer and Mindel C. Sheps, is performed in the following manner:

3 rabbits are used per test. The animals are narcotized with Nembutal; after an additional local anesthesia the heart-side vena jugularis is laid open, two ligatures being prepared at a distance of 1 to 2 cm.

The preparation to be tested is now injected within 15 seconds in the desired dosis into the ear vein opposite the vena jugularis laid open. Within 10 to 25 seconds after the injection of the preparation the prepared ligatures are contracted. The isolated vein segment now remains in situ in the rabbit for 10 minutes. Then the vein section is removed from the animal and dissected in a Petri dish in a 5% sodium citrate solution, the contents being evaluated according to the following scheme.

0 = no clot
1 = few macroscopically visible fibrin particles
2 = some small thrombi
3 = two or more large thrombi
4 = one single thrombus filling up the entire isolated vein segment.

The test is valued positive in the case of a 4-reaction. It is essential for the preparation according to the invention that upon injection of the preparation, which contains at least 2 units of FEIBA per kg of experimental animal, no 4-reaction takes place.

The determination of the kallikrein activity and the prekallikrein activator activity is carried out in the following way.

KALLIKREIN

1. Method:

Kallikrein amidolytically splits para-nitroanilin (pNA) from a specific chromogenic substrate. The concentration of pNA is photometrically measured at a wave length of 405 nm.

2. Reagents:
Buffer:

Solution A: 3.03 g "TRIS" and 1.7 g imidazole are dissolved in 500 ml 0.1 n hydrochloric acid and water is added up to 1,000 ml.
Solution B: 4.04 g "TRIS" and 2.27 g imidazole are dissolved in 500 ml 0.1 n hydrochloric acid and water is added up to 1,000 ml.
Solution C: 11.69 g of sodium chloride are dissolved with water to 1,000 ml.

Solutions A and B are mixed until a pH of 7.9 is reached. To this mixture the same volume of solution C is added.

Chromogenic substrate S-2302 (Kabi, Stockholm): H-D-prolyl-L-phenylalanyl-L-arginine-p-nitroanilid-dihydrochloride 1 millimolar solution of S-2302: 25 mg in 41 ml of water. Sample:

The sample is dissolved in the original volume and used in the test undiluted.

3. Test:
In a water bath at a temperature of 37° C.

1.0 ml buffer preheated to 37° C.
0.1 ml sample
0.2 ml chromogenic substrate S-2302 are pipetted into a plastic tube. This mixture is charged into a photometer heated to 37° C. and the increase of the optical density per minute ($\Delta OD/min$) at the wave length of 405 nm with a path length of 10 mm is measured. The activity of a sample is expressed in $\Delta OD/min$.

PREKALLIKREIN ACTIVATOR

1. Method:

From a purified prekallikrein preparation (PKK) kallikrein (KK) is generated by means of a prekallikrein activator (PKKA). The kallikrein amidolytically splits para-nitroaniline (pNA) from a specific chromogenic substrate. The concentration of pNA is photometrically measured at a wave length of 405 nm.

2. Reagents:

Buffer and chromogenic substrate correspond to the reagents described in connection with the kallikrein determination.

Prekallikrein preparation:

The production of the preparation is effected according to a prescription of Harpel, modified by M. S. Horowitz (New York Blood Center). Therein human citrated plasma is treated with a DEAE-cellulose. The fraction that is not bound to the DEAE-cellulose contains the prekallikrein.

Positive control (standard):

As standard (=reference value) an albumin preparation of the Bureau of Biologics (BoB) of the Food and Drug Administration, Bethesda, Md. 20205, U.S., is used. This preparation contains a prekallikrein activator. The kallikrein generation with this BoB-standard represents the reference value 1 and is equated with 100%.

Sample:

The sample is dissolved in the original volume and used in the test undiluted.

3. Test:
In a water bath at a temperature of 37° C.

0.05 ml prekallikrein preparation
0.05 ml sample
  (a) BoB-standard for the reference value
  (b) test sample (in a second test mixture)
are pipettet into a plastic tube. After an incubation of 10 minutes at 37° C.

0.7 ml buffer solution
0.1 ml chromogenic substrate S-2302 are pipetted. This mixture is charged into a photometer heated to 37° C. and the increase in the optical density per minute ($\Delta OD/min$) is measured at a wave length of 405 nm with a path length of 10 mm. The activity of a sample ($\Delta OD/min$) is expressed in % of the Bob-standard.

The characterization of the preparation according to the invention by an affinity-chromatographic separation of the preparation on dextran sulphate sepharose has already been described in connection with FIG. 1.

The electrophoretic separation of the proteins with factor IX activity and with FEIB-activity, which is referred to in connection with FIG. 2, can be carried out in the following manner.

As the carrier for the electrophoretic separation of the various proteins a cellulose-acetate membrane serves, which is wetted with the electrophoresis buffer (pH 8.6, ionic strength 0.075). On this membrane the samples to be analyzed—together with a normal human plasma as standard—are applied and then separated in the electric field; the separation is effected in that differently charged proteins migrate at different speeds in the electric field. To this end the membrane provided with the samples is treated in a special cell filled with the electrophoresis buffer for 16 to 18 minutes at a voltage of 250 volts and an initial current intensity of 4 to 6 milliamperes.

After termination of the separation procedure the various proteins are rendered visible by putting the membrane into a fixing and dyeing solution. After some rinsing baths the membrane is made transparent in a further bath, applied onto a glass plate and dried in a drying chamber at 100° C.

The dried membrane is then analyzed in an automatically registering and integrating densitometer, which produces separation curves as illustrated in FIG. 2. The various proteins appear as different peaks whose areas are proportional to the relative percentage values of the corresponding proteins, these areas being determined by the automatic integration of the densitometer.

The allocation of the various peaks or proteins of the test sample to defined proteins or protein groups is effected by comparing them with the peaks of the normal human plasma simultaneously analyzed as standard. During the electrophoretic analysis the latter is separated into 5 protein groups, which by definition are designated as follows—in the order of decreasing mobility in the electric field: albumin, $\alpha$-globulins, $\beta$-globulin, fibrinogen, and $\gamma$-globulin.

The definition of the FEIBA unit as well as its determination (potency test) is described in U.S. Pat. No. 4,160,025.

The determination of the activity of the coagulation factors II, VII, IX and X is also described in the above-mentioned U.S. Pat. No. 4,160,025.

The determination of the residual activity of FEIBA after incubation in factor VIII inhibitor plasma is carried out in the following manner.

1. Reagents:

The reagents to be used are described in U.S. Pat. No. 4,160,025 in connection with the determination of the FEIBA units (potency test).

2. Test:

From a preparation adjusted to 50 FEIBA units/ml the following dilutions are prepared with a solution of 7 g/l sodium chloride and 7 g/l sodium citrate. 0.2H$_2$O as diluent: 1:2, 1:4, 1:8, 1:16, 1:32 and 1:64.

From these 6 dilutions a 1:10 dilution in factor VIII inhibitor plasma (0.05 ml pre-diluted sample+0.45 ml factor VIII inhibitor plasma) each is prepared.

These 1:10 dilutions in factor VIII inhibitor plasma ("incubation mixtures") are then analyzed immediately and after one hour of incubation at 37° C. according to the following test scheme:

0.1 ml "incubation mixture"
0.1 ml phospholipid-kaolin suspension incubation at 37° C. for 1 minute
0.1 ml m/40 calcium chloride.

The time from the addition of calcium chloride to the clot formation is taken with a timer like in the potency test.

3. Calculation of the residual activity:

Analogously to the description in the potency test, a calibration curve is established with the coagulation times of the immediately determined dilutions (undiluted sample=5 FEIBA units/ml). The activities (FEIBA units/ml) of the various dilutions incubated for one hour are then calculated by using the calibration curve and are expressed in percent of the individual activities of the non-incubated dilutions. The mean values of the activities thus calculated produce the average residual activity of the sample after an hour of incubation, expressed in percent of the initial activity prior to incubation.

The determination of the residual activity of factor IX after incubation in factor IX deficient plasma is carried out in the following manner:

1. Reagents:

Factor IX deficient plasma: citrated plasma of a patient suffering from severe haemophilia B (factor IX below 1%). Phospholipid/kaolin suspension: PTT reagent of Immuno Diagnostica Ges.m.b.H. For the test the required amount of factor IX deficient plasma is mixed with an equal volume of the phospholipid/kaolin suspension, incubated for 5 minutes at 37° C. and then stored in an ice bath during the test period.

Citrate/saline solution as diluent for samples: 7 g/l trisodium citrate.2H$_2$O, 7 g/l sodium chloride.

Calcium chloride m/20 (0.05 molar): storing at 37° C. during the test period.

2. Test:

From a preparation adjusted to 50 factor IX units/ml 7 geometric dilutions (1:2, 1:4 etc. until 1:128) are prepared with the citrate/saline solution. From the undiluted sample as well as from the 7 geometric dilutions a 1:10 dilution in factor IX deficient plasma is each prepared (0.05 ml prediluted sample+0.45 ml factor IX deficient plasma).

These 1:10 dilutions in factor IX deficient plasma ("incubation mixtures") are then analyzed immediately and after an hour of incubation at 37° C. according to the following test scheme, each incubation mixture being diluted 1:10 with the citrate/saline solution prior to determination:

0.2 ml mixture of factor IX deficient plasma and phospholipid/kaolin
0.1 ml "incubation mixture", 1:10 diluted with citrate/saline solution incubation at 37° C. for 1 minute
0.1 ml m/20 calcium chloride The time from the addition of calcium chloride to the clot formation is taken by a timer.

3. Calculation of the residual activity:

A calibration curve is established with the coagulation times of the immediately determined dilutions (undiluted sample=50 factor IX units/ml) by plotting the coagulation times against the corresponding dilutions on double logarithmic graph paper. The activities (factor IX units/ml) of the various dilutions incubated for one hour are then calculated by using the calibration curve and are expressed in percent of the respective activities of the non-incubated dilutions. The mean values of the activities thus calculated produce the average residual activity of the sample after one hour of incubation, expressed in percent of the initial activity prior to incubation.

Immunologic determination of the inter-alpha-trypsin-inhibitor (ITI):

1. Method:

The determination is effected according to the Ouchterlony-technique, wherein a specific antibody diffuses in an agar medium against an antigen-containing sample. The antigen specifically reacts with the antibody, forming an immune precipitation peak that is valued as positive reaction.

2. Reagents:

Rabbit antiserum against ITI, Behringwerke AG, Marburg/Lahn, BRD

Agar: A solution of 1.25 g agar, 0.9 g sodium chloride and 100 mg sodium azide in 100 ml water is briefly boiled, and the hot homogeneous solution is poured into plates yielding a layer of about 2 mm thickness. Into the cooled solidified gel holes having a size of about 2 mm are punched in two rows at a distance of 5 mm.

Standard and sample:

As calibration substance a protein standard serum of Behringwerke with a defined content in ITI serves. From this reference serum a geometric dilution series in a physiologic sodium chloride solution (9 g NaCl/l) is prepared. The sample to be tested is treated like the standard.

3. Test:

Into one hole row of the agar the dilutions of the calibration substance or sample to be tested are charged, in the adjacently arranged hole row the undiluted specific antiserum is pipetted. The agar plate thus charged is incubated at 37° C. for 15 hours. Afterwards the reading of the immune precipitations is effected.

4. Calculation of the ITI-concentration:

As a measure for the ITI-concentration of a sample the dilution step is chosen at which a precipitation is just visible ("titer" of the sample). The ITI-concentration of the sample to be tested is calculated as follows:

$$\frac{\text{titer of test sample}}{\text{titer of standard}} \times \textit{ITI}\text{-concentration of standard}.$$

The ITI-concentration is indicated in mg % (mg/100 ml).

The preparations produced according to Examples 1 and 2 were analyzed according to the preceding assay methods; the results are summarized in the following Table.

The illustrations in FIG. 1 (affinity-chromatographic separation) and FIG. 2 (electrophoretic separation) of the drawings correspond to the data of Example 2 in the following Table.

TABLE

| | FEIBA preparation produced according to | |
|---|---|---|
| | Example 1 | Example 2 |
| FEIBA units/ml | 26.0 | 24.2 |
| Factor II units/ml | 25.8 | 23.0 |
| Factor VII units/ml | 24.0 | 26.5 |
| Factor IX units/ml | 28.2 | 27.4 |
| Factor X units/ml | 24.1 | 22.1 |
| Thrombogenic activity in the Wessler test: | | |
| free of thrombogenic effect up to a dosage of | 10 FEIBA units/kg | 4 FEIBA units/kg |
| Affinity-chromatography on dextran suphate sepharose (agarose) | | |
| Factor IX activity eluted at | 0.14–0.49 m NaCl | 0.13–0.50 m NaCl |
| Maximum factor IX activity eluted at | 0.31 m NaCl | 0.30 m NaCl |
| FEIB-activity eluted at | 0.33–0.49 m NaCl | 0.31–0.50 m NaCl |
| Maximum FEIB-activity eluted at | 0.41 m NaCl | 0.40 m NaCl |
| Electrophoretic separation of the protein with factor IX and FEIB-activity | | |
| α-globulin, main peak | 67% | 70% |
| α-globulin, shoulder | 16% | 14% |
| β-globulin | 17% | 16% |
| Kallikrein activity | 0 | 0 |
| Prekallikrein activator activity | 0 | 0 |
| % Residual activity of FEIBA after 1 hour incubation in factor VIII inhibitor plasma | 65% | 57% |
| % Residual activity of factor IX after 1 hour incubation in factor IX deficient plasma | 60% | 55% |
| Inter-alpha-trypsin inhibitor | 0.6 mg/FEIBA unit | 0.2 mg/FEIBA unit |

What we claim is:

1. A blood-coagulation-promoting preparation based on human proteins, having a content of coagulation factors II, VII, IX and X and factor-VIII-inhibitor-bypassing-activity (FEIBA), which preparation is characterized in that it is free of thrombogenic activity up to at least 2 units of FEIBA per kg rabbit in the thrombosis inducing activity test according to Wessler, it is free of kallikrein activity and free of prekallikrein activator activity, measured in an aqueous solution of said preparation with a FEIBA concentration of up to at least 10 units per ml, it is affinity-chromatographically separable on dextran sulphate agarose by means of an NaCl gradient so as to obtain an eluate containing a protein with factor IX activity and an eluate containing a protein with FEIB-activity, said protein with factor IX activity eluting at a lower NaCl concentration than said protein with FEIB-activity, said eluate containing said protein with factor IX activity and said eluate containing said protein with FEIB-activity contain α- and β-globulins when electrophoretically separated thus obtaining a separation curve having a main peak in the α-globulin region corresponding to a content of 60 to 80% of the total protein, a shoulder of 10 to 20% of the total protein following thereupon, and a slightly pronounced peak in the β-globulin region corresponding to a content of 10 to 20% of the total protein following upon the shoulder-like course of said separation curve.

2. A preparation as set forth in claim 1, wherein said protein with factor IX activity elutes at an NaCl concentration of 0.1 to 0.5 molar and said protein with FEIB-activity elutes at an NaCl concentration of 0.3 to 0.5 molar, the maximum factor IX activity eluting at 0.3 molar and the maximum FEIB-activity eluting at 0.4 molar.

3. A preparation as set forth in claim 1, wherein said FEIB-activity, after a one-hour incubation in factor VIII inhibitor plasma, is preserved by at least 50%.

4. A preparation as set forth in claim 1, wherein said factor IX activity, after a one-hour incubation in factor IX deficient plasma, is preserved by at least 50%.

5. A preparation as set forth in claim 1, further comprising a content of inter-alpha-trypsin inhibitor (ITI) of 0.05 to 5 mg per FEIBA unit.

6. A method of producing a blood-coagulation-promoting preparation as set forth in claim 1, which method comprises treating human plasma with sulphated high-polymer carbohydrates and/or with basic ion exchangers so as to obtain a protein mixture with generated FEIB-activity, adsorbing said protein mixture, and recovering said preparation by elution and concentration.

7. A method as set forth in claim 6, wherein said human plasma at first is briefly treated with sulphated high-polymer carbohydrates, said protein mixture with generated FEIB-activity is then adsorbed on an ion exchanger on dextran basis and is then immediately eluted and concentrated.

8. A method as set forth in claim 6, wherein said human plasma is treated with an ion exchanger on dextran basis, and after at least two hours of exposure said protein mixture with generated FEIB-activity, adsorbed on said ion exchanger, is eluted and concentrated.

9. A method for promoting the coagulation of blood containing an inhibitor to factor VIII which comprises administering to a patient having blood which contains an inhibitor to factor VIII, an amount, effective to provide factor-VIII-inhibitor-by-passing-activity, of a blood coagulation-promoting preparation, which is produced according to the method described in claim 6.

10. A blood-coagulation-promoting preparation based on human proteins, having a content of coagulation factors II, VII, IX and X and a factor-VIII-inhibitor-by-passing-activity (FEIBA), which preparation is characterized in that it is free of thrombogenic activity up to at least 2 units of FEIBA per kg rabbit in the thrombosis inducing activity test according to Wessler; it is free of kallikrein activity and free of prekallikrein activator activity, measured in an aqueous solution of said preparation with a FEIBA concentration of up to at least 10 units per ml; and it is affinity-chromatographically separable on dextran sulphate agarose by means of an NaCl gradient so as to obtain an eluate containing a protein with factor IX activity and an eluate containing a protein with FEIB-activity, said protein with factor IX activity eluting at a lower NaCl concentration than said protein with FEIB-activity.

11. A preparation as set forth in claim 10, wherein said FEIB-activity, after a one-hour incubation in factor VIII inhibitor plasma, is preserved by at least 50%.

12. A preparation as set forth in claim 10, further comprising a content of inter-alpha-trypsin inhibitor (ITI) OF 0.05 to 5 mg per FEIBA unit.

13. A method for promoting the coagulation of blood containing an inhibitor to Factor VIII, which comprises administering to a patient having blood which contains an inhibitor to factor VIII, an amount, effective to provide factor-VIII-inhibitor-bypassing activity, of a blood coagulation-promoting preparation based on human proteins, having a content of coagulation factors II, VII, IX and X and factor-VIII-inhibitor-bypassing-activity (FEIBA), which preparation is characterized in that it is free of thrombogenic activity up to at least 2 units of FEIBA per kg rabbit in the thrombosis inducing activity test according to WEssler; it is free of kallikrein activity and free of prekallikrein activator activity, measured in an aqueous solution of said preparation with a FEIBA concentration of up to at least 10 units per ml; and it is affinity-chromatographically separable on dextran sulphate agarose by means of an NaCl gradient so as to obtain an eluate containing a protein with factor IX activity and an elute containing a protein with FEIB-activity, said protein with factor IX activity eluting at a lower NaCl concentration than said protein with FEIB-activity, said eluate containing said protein with factor IX activity and said eluate containing said protein with FEIB-activity contain α- and β-globulins when electrophoretically separated thus obtaining a separation curve having a main peak in the α-globulin region corresponding to a content of 60 to 80% of the total protein, a shoulder of 10 to 20% of the total protein following thereupon, and a slightly pronounced peak in the β-globulin region corresponding to a content of 10 to 20% of the total protein following upon the shoulderlike course of said separation curve.

14. A method for promoting the coagulation of blood containing an inhibitor to factor VIII, which comprises administering to a patient having blood which contains an inhibitor to factor VIII, an amount, effective to provide factor-VIII-inhibitor-bypassing-activity, of a blood coagulation-promoting preparation based on human proteins, having a content of coagulation factors II, VII, IX and X and factor-VIII-inhibitor-by-passing-activity (FEIBA), which preparation is characterized in that it is free of thrombogenic activity up to at least 2 units of FEIBA per kg rabbit in the thrombosis inducing activity test according to Wessler; it is free of kallikrein activity and free of prekallikrein activator activity, measured in an aqueous solution of said preparation with a FEIBA concentration of up to at least 10 units per ml; and it is affinity-chromatographically separable on dextran sulphate agarose by means of a NaCl gradient so as to obtain an eluate containing a protein with factor IX activity and an elute containing a protein with FEIB-activity, said protein with factor IX activity eluting at a lower NaCl concentration than said protein with FEIB-activity.

* * * * *

UNITED STATES PATENT AND TRADEMARK OFFICE
CERTIFICATE OF CORRECTION

PATENT NO. : 4,395,396
DATED : July 26, 1983
INVENTOR(S) : Eibl et al.

It is certified that error appears in the above—identified patent and that said Letters Patent is hereby corrected as shown below:

Col. 1, line 45, "ky" should read --kg--. Col. 2, line 1, "resposible" should read --responsible--. Col. 4, line 38, "unit" should read --units--. Col. 6, line 46, "pipettet" should read --pipetted--. Col. 7, line 54, "each is" should read --is each--. Col. 8, line 4, "5" should read --50--; lines 32-33, "unidiluted" should read --undiluted--. Col. 9, line 38, "into" should read --onto--. Col. 10, 11th line of TABLE, "suphate" should read --sulphate--. Col. 12, line 25, "elute" should read --eluate--; line 57, "elute" should read --eluate--.

Signed and Sealed this

Eighth Day of November 1983

[SEAL]

Attest:

GERALD J. MOSSINGHOFF

Attesting Officer     Commissioner of Patents and Trademarks